United States Patent [19]

Stanley, Jr., deceased et al.

[11] Patent Number: 5,744,564
[45] Date of Patent: Apr. 28, 1998

[54] WRINKLED ABSORBENT PARTICLES OF HIGH EFFECTIVE SURFACE AREA HAVING FAST ABSORPTION RATE

[75] Inventors: Frederick W. Stanley, Jr., deceased, late of Midland, by Caroline Stanley, legal representative; Jack C. Lamphere, Midland; Larry R. Wilson, Beaverton, all of Mich.

[73] Assignee: The Dow Chemical Company, Midland, Mich.

[21] Appl. No.: 140,182

[22] PCT Filed: Aug. 28, 1992

[86] PCT No.: PCT/US92/07336

§ 371 Date: Nov. 4, 1993

§ 102(e) Date: Nov. 4, 1993

[87] PCT Pub. No.: WO93/19099

PCT Pub. Date: Sep. 30, 1993

[30] Foreign Application Priority Data

Mar. 14, 1992 [DE] Germany ............... 921 04 434.3

[51] Int. Cl.$^6$ ........................................... C08F 2/32
[52] U.S. Cl. ........................... 526/317.1; 526/349.7
[58] Field of Search ................... 526/81, 317.1, 526/329.7

[56] References Cited

U.S. PATENT DOCUMENTS

| | | | |
|---|---|---|---|
| 4,037,040 | 7/1977 | Trapasso | 526/88 |
| 4,340,706 | 7/1982 | Obayashi | 526/207 |
| 4,446,261 | 5/1984 | Yamasaki | 524/40 |
| 4,578,068 | 3/1986 | Kramer | 604/368 |
| 4,600,458 | 7/1986 | Kramer | 156/199 |
| 4,666,983 | 5/1987 | Tsubakimoto | 525/119 |
| 4,683,274 | 7/1987 | Nakamura | 526/216 |
| 4,739,008 | 4/1988 | Robinson | 524/801 |
| 4,742,086 | 5/1988 | Masamizu | 521/62 |
| 4,757,091 | 7/1988 | Hawrylko | 526/81 |

FOREIGN PATENT DOCUMENTS

| | | |
|---|---|---|
| 9008789 | 8/1990 | WIPO . |
| 9015829 | 12/1990 | WIPO . |
| 9216565 | 10/1992 | WIPO . |

*Primary Examiner*—Thomas R. Weber

[57] ABSTRACT

The subject invention pertains to large particle size, attrition-resistant, continuous, but wrinkled, high surface area aqueous fluid absorbent polymers, preferably of a crosslinked acrylic acid or acrylate. These absorbents have absorption rates superior to spherical absorbents. The subject invention further pertains to a process of preparing such polymers comprising suspension polymerization with an at least partially off phase soluble initiator. The subject invention further pertains to absorbent structures containing such polymers and to the use of such polymers therein.

39 Claims, 5 Drawing Sheets

WRINKLED ABSORBENT PARTICLES OF HIGH EFFECTIVE SURFACE AREA HAVING FAST ABSORPTION RATE

The present invention relates to absorbents formed of water insoluble, typically gel-forming, polymeric materials that are capable of, for example, absorbing many times their own weight upon contact with aqueous fluids. More particularly, the present invention focuses upon polymeric materials that absorb substantial volumes of such fluids at a high rate of absorption, processes for making them, uses thereof in absorbent articles, and absorbent articles incorporating such polymeric materials.

Many water insoluble gel-forming polymers are known for their usefulness as absorbents because of their ability to imbibe and bind or immobilize aqueous fluids. These polymeric materials find employment in industry for various dewatering and fluid immobilization uses, such as water retaining agents in agricultural/horticultural fields, dehydration of oil, and like purposes. In recent years absorbent polymers having large capacities for absorbing aqueous fluids have been developed and have found use in personal care products for absorbing aqueous biological fluids. In a typical personal care product, such as a diaper, the aqueous fluid absorbent polymer is utilized in powder form, and is often mixed with cellulosic fibers that help initially absorb and distribute the fluid load. The polymeric materials of interest in such products are based upon a variety of polymers including those derived from water soluble ethylenically unsaturated monomers or graft polymers in which unsaturated monomers are graft polymerized onto a polysaccharide (such as starch or cellulose) or other polymeric backbone.

A preferred absorbent material is derived from a water insoluble gel formed by copolymerizing an ethylenically unsaturated carboxylic acid with a multifunctional crosslinking monomer. The acid monomer or polymer is substantially neutralized with an alkali metal hydroxide, dried and pulverized into a powder form before use in a personal care product. A preferred polymer gel is a copolymer of acrylic acid/sodium acrylate and any of a variety of crosslinkers.

Achieving desired polymeric characteristics that provide superior performance in a personal care product has long been a challenging goal of researchers. The product must perform for the user but also must be capable of being economically and safely made. At the customer/user level, a diaper, for example, most desirably must keep the user substantially dry, even in response to repeated wettings. Thus, a key desired characteristic of an aqueous fluid absorbent polymer, at least for diaper use, is that it have high fluid capacity, e.g., a centrifuge capacity greater than 10 grams/gram. In addition, a most desired characteristic of the aqueous fluid absorbent polymer is that it has a fast rate of absorption, adequate to imbibe and hold the fluid during absorption without leakage of fluid from the device in which it is employed. It is adequate fast rate, while maintaining all of the other desired qualities of the aqueous absorbent, that has eluded prior researchers.

It is well-known in the prior art that the rate of fluid absorbency is substantially determined by the surface area of the particles. Thus, extremely fine particles of aqueous fluid absorbent, those less than 100 mesh (149 micrometers), would be expected to absorb liquids at a rapid rate. However, the individual particles at the surface of the polymeric mass of such fines initially contacted by the fluid rapidly swell and adhere together, drastically reducing the rate of absorption as the fluid is "gel blocked" from access to particles of absorbent in the mass that are more remote from the surface. Lumps or "fish eyes" often form such that overall performance of the absorbent material is unsatisfactory.

An additional difficulty with fine materials is that such fines create dusting problems in manufacturing and forming into finished articles. Fines or dusts may be a source of industrial hygiene risks for workers as well as pose difficult materials handling problems. At the product level it may be difficult to immobilize fine particulate materials in the article or device of interest without elaborate containment structures that increase costs and may limit the ability of the article to perform at a desired level.

A number of workers have attempted to produce a non-dusting and/or fast absorbency rate product by making somewhat larger particles that still possess useful absorbency, changing polymer particle surface characteristics or adhering fines particles together. The balancing of desirable product end-use qualities with manufacturing limitations has heretofore meant accepting one or more less desirable characteristics.

Yamasaki, et al. in U.S. Pat. No. 4,446,261 describes making a larger sized particle that avoids dusting and is said to have improved capacity and absorbency rate over the prior art. The process produces resin particles by means of a suspension polymerization process, including a water-soluble redox initiator system, that utilizes oil soluble cellulose ester or cellulose ether as a protecting colloid in order to obtain spherical particles of a size that do not cause dusting. However, while stating that the beads have a fast absorbency rate over the prior known suspension processes, only absorbency rates greater than 4 minutes for 0.5 grams of polymer to absorb 5 milliliters of saline solution, are reported.

A number of researchers have worked at improving absorption rates for water absorbent resins. Nakamura, et al. in U.S. Pat. No. 4,683,274 suggests rate improvements for $\alpha,\beta$-unsaturated carboxylic acid based polymers produced by inverse emulsion polymerization through inclusion of a sucrose fatty acid ester as a protective colloid agent. Water absorption rates are said to improve to about 1 minute from 15 minutes for the time required for 1 gram of resin to absorb 30 milliliters of 0.9 percent aqueous sodium chloride solution. Such improvements, while substantial, are still not sufficient for many personal care product uses.

In GB 2119384A, crosslinking the surface layer of a specific water absorbing resin having a carboxyl group with a polyhydric alcohol is said to minimize fines and gel blocking. However, while the improvement reported is significant, much higher absorption rates are still desired.

In agglomeration of fines techniques, maintaining adequate absorbency generally requires that the degree of adherence or binding of the fines particles together be limited, similar to the well-known limits on crosslinking. Otherwise, fused particles are formed that may result in products that still gel-block. Limiting binding of the particles together generally produces agglomerated products that tend to be easily attrited during incorporation into finished articles, recreating the dusting problems. Attrition may also occur in the finished product such that fines block distribution of fluid in an article by filling in channels and spaces in a fiber matrix.

It appears clear from the difficulties of making an agglomerated product that a desirable absorbent polymer particulate, especially for use in personal care products applications, remains a discreet large-sized particle, if, in contrast to the prior art, adequate absorbent capacity and rate could be achieved. While large particle sized absorbents have been made, as noted above, they simply heretofore have not possessed adequate rates of absorbency. Thus, it remains desirable to provide an absorbent polymer that is a discreet non-agglomerated particulate that has high absorbent capacities, does not gel block and has a fast rate of absorbency, i.e., a vortex rate of 1 minute or less.

The present invention is a fluid absorbent polymer having a fast rate of absorption for aqueous fluids, comprising individual polymer particles each having a high surface area, each said particle surface substantially continuous but including a plurality of wrinkles comprising folds, ridges, crevices, and channels. The polymer particles are swellable such that a fluid in contact with said particles is effectively exposed to a substantial portion of the surface area of said particles for absorption of said fluid. The wrinkles of the invention, including folds, ridges, crevices, and channels, are further characterized and depicted in FIGS. 1 through 4. The resulting product has a rate of absorption of less than one minute, preferably less than 20 seconds, as measured by a "vortex test" described below. The particle size of the fluid absorbent polymer particles is substantially greater than 75 micrometers in diameter, preferably greater than 100 micrometers.

The invention also includes a method for making the fast rate aqueous fluid absorbent of the invention, comprising:

suspending a water soluble monomer mixture in a continuous, inert, organic liquid phase, containing suspending agents, with agitation such that droplets of said monomer mixture form in said continuous phase;

adding to said suspension an oxidizing component of a redox initiator pair, said reducing component at least partially soluble in the organic liquid phase; and introducing a reducing component of said redox pair into said organic phase under polymerizing conditions at a controlled rate such that said polymer particles having wrinkled surfaces form.

The invention also includes the use of the fluid absorbent polymer of the invention in an article for absorbing biological fluids. The invention includes such use wherein the article is a disposable diaper.

The invention also includes an absorbent article comprising a hydrophilic fiber material and any of the polymers of the invention. The absorbent article preferably further comprises a fluid impervious bottom layer and a fluid pervious top layer, said absorbent article being retained between said bottom layer and said top layer; said absorbent article being further characterized as containing between 20 and 98 weight percent of said hydrophilic fiber material and between 2 and 80 weight percent of any of said polymers of the invention.

The absorbent polymer of the invention are particularly useful in forming personal care articles for absorbing biological fluids, such as disposable diapers.

BRIEF DESCRIPTION OF THE DRAWINGS

A key element of the invention is a high surface area aqueous absorbent polymer particle that is characterized by a continuous but wrinkled surface and an exceptionally high rate of absorbency for aqueous fluids, in comparison with conventional spherical absorbent materials. Referring to the Figures, FIGS. 1–4 are photomicrographs of the polymer particles of the invention, at a magnification of 50, for a crosslinked polymer based upon acrylic acid, as further described in the examples below. Each polymer particle is also shown in cross section which further suggests its uniqueness and exceptionally high surface area of the resin available for absorbing aqueous fluids. Herein, the phrase "particle surface substantially continuous but including a plurality of wrinkles comprising folds, ridges, crevices, and channels" is defined to mean the surface morphology depicted in FIGS. 1–4.

Figure 1A:
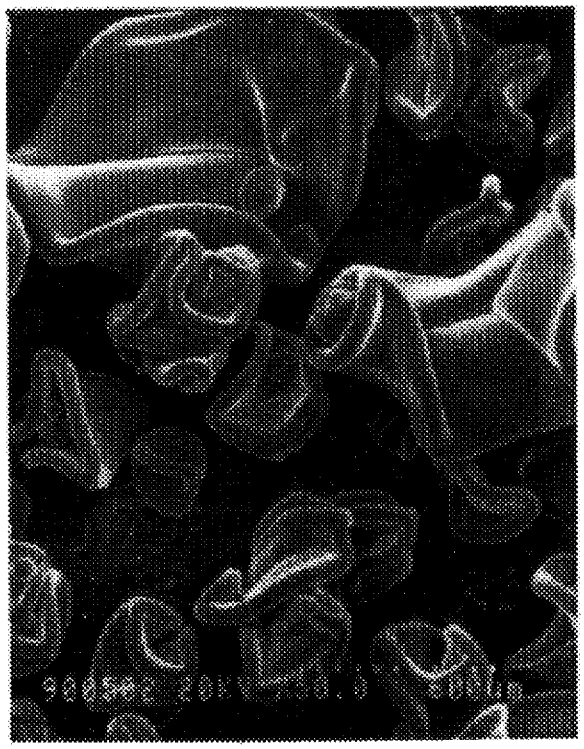
FIG. 1(a) is a photomicrograph at a magnification of 50 of the polymer particles of the invention wherein the initial monomer mixture comprises 24 percent acrylic acid.

The polymer particles of the invention have a high surface area. Preferred areas are between 0.3 and 0.5 $m^2/g$. An especially preferred surface area is 0.3 $m^2/g$.

The high surface area polymer of the invention is made by means of a suspension polymerization process of the invention. A key feature of the process of the invention for making the high surface area, high absorbency rate polymer, is that polymerization of the discontinuous phase monomer droplets suspended in a continuous oil phase is initiated in the continuous oil phase by means of an initiator that is at least partially oil phase soluble. This is in contrast to conventional suspension polymerizations which generally employ initiators soluble in the aqueous phase.

Generally, the monomer droplets must be of a certain minimum size for adequate wrinkling to occur. It is preferred that the monomer droplets be larger than 75 micrometers in diameter at initiation of the polymerization. More preferably, the monomer droplets will be between 75 and 1000 micrometers in diameter, most preferably between 150 and 1000 micrometers, and most preferably with an average diameter of 400 micrometers at the initiation of polymerization.

The water absorbent compositions of the invention may be made from a variety of polymers or copolymers. Basically, any water-soluble ethylenically unsaturated monomer or mixture thereof that crosslinks to form a substantially water insoluble gel or particle is suitable. Crosslinked structures may be obtained by the copolymerization of a water-soluble monomer and a crosslinking monomer possessing at least two polymerizable double bonds in a molecular unit, as is well-known in the art. Monomer mixtures that include graft, as well as addition polymerizing systems may be employed so long as the wrinkled surface can be imparted to the resulting polymer or copolymer particles.

Exemplary water-soluble monomers include ethylenically unsaturated amides such as acrylamide, methacrylamide, and fumaramide as well as their N-substituted derivatives. Ethylenically unsaturated carboxylic acids such as acrylic, methacrylic, and crotonic acids and their salts are preferred. Suitable polycarboxylic acids include maleic acid and fumaric acids and itaconic acid. Preferred ethylenically unsaturated carboxylic acid esters include hydroxyethylacrylate, hydroxyethylmethacrylate, and esters of acrylic and methacrylic acids with polyethylene oxide. Vinyl amines such as vinyl pyridine and vinyl morpholine, and diallyl amines are also useful. Other suitable monomers are well known to those skilled in the art as discussed in U.S. Pat. No. 4,708,997.

The ethylenically unsaturated monomer may be partially neutralized as set forth below. In such cases, the monomer mixture will further comprise the salt of the ethylenically unsaturated monomer. The monomer mixture may also include components that graft polymerize onto one or more other monomer additional monomers of the monomer mixture. Polysaccharides, such as starch and cellulose are examples of graft-polymerizable components. Particularly suitable is a graft-polymerizable polyvinyl alcohol.

The concentration of monomer in the monomer mixture used to make the wrinkled particles of the invention is a key factor in determining the degree of wrinkling achieved. The effect of concentration of monomer, of course, depends upon the particular system of interest. In the preferred acrylic acid/sodium acrylate system, varying the concentration of acrylic acid monomer in the initial monomer mixture, has a profound effect upon the degree of wrinkling, as demonstrated by FIGS. 1–4, wherein the concentration of monomer varies between 24 and 33 weight percent. For the acrylic acid/sodium acrylate system at least about 10 percent acrylic acid in the initial monomer mixture (prior to neutralization) is required to achieve useful wrinkling, useful at least from an economic view. Preferably, the initial monomer mixture will contain from 10 to 50 percent acrylic acid, more preferably from 24 to 35 percent acrylic acid.

The suspension polymerization of the present invention, when carboxylic acid monomers are employed, generally provides that the monomers be neutralized at least partially prior to the polymerization. Preferably, the acid monomers will be between 75 and 95 percent neutralized, more preferably between 80 and 90 percent neutralized. The neutralization is generally carried out, as is well known in the art, by simply mixing the monomers, including any crosslinking agents, with any suitable base, e.g. an alkali hydroxide such as sodium hydroxide or potassium hydroxide or an alkali carbonate or bicarbonate such as sodium or potassium carbonate or bicarbonate, as the initial step of the process of preparation of the polymers of the invention. The neutralization is advantageously carried out at temperatures below about 40° C., preferably below about 35° C.

The monomer mixture typically includes one or more crosslinking monomers which comprise organic compounds having two or more ethylenic groups copolymerizable with the water-soluble monomers of the monomer mixture. Exemplary crosslinking monomers include diacrylate or dimethacrylate of ethylene glycol, diethylene glycol, triethylene glycol, tetraethylene glycol, propylene glycol, 1,4-butane diol, 1,5-pentane diol, 1,6-hexane diol, neopentyl glycol, trimethylol propane and pentaerythritol; triacrylates or trimethacrylates of trimethylol propane and pentaerythritol tetracrylates or tetramethacrylates of pentaerythritol, N,N'-methylene-bis-acrylamide; N,N'-methylene-bis-methacrylamide; and triallyl isocyanurate. Preferred crosslinkers include methylene-bis-acrylamide, trimethylol propanetriacrylate and diethylene glycol diacrylate and tetraethylene glycol diacrylate. Crosslinking monomers are present in the dispersion of water-soluble monomer in an amount effective to crosslink the water-soluble polymer. Typically, the crosslinking monomer is used in amounts ranging from about 0.0001 to about 5 parts by weight, based on 100 parts by weight of the water-soluble monomer used.

In the suspension polymerization process of the invention, the monomer mixture is suspended in an inert organic phase or oil phase comprising an organic material that is non-reactive with the monomers and resulting products. The water-immiscible oil phase of the suspension generally comprises as least one inert hydrophobic liquid, such as a liquid hydrocarbon or substituted liquid hydrocarbon. Preferred organic liquids are the halogenated hydrocarbons such as perchloroethylene, methylene chloride, and liquid hydrocarbons having 4 to 15 carbon atoms per molecule, including aromatic and aliphatic hydrocarbons and mixtures thereof such as benzene, xylene, toluene, mineral oils, liquid paraffins such as kerosene, and naphtha. Of the foregoing organic liquids, the hydrocarbons are the more preferred, with the aliphatic hydrocarbons being most preferred. A preferred commercially available aliphatic hydrocarbon is ISOPAR® M deodorized kerosene, sold by Exxon.

The inert organic or oil phase includes dispersing agents to keep the aqueous soluble monomer droplets suspended in an oil phase for the suspension polymerization. These dispersing agents include surface active materials such as sucrose fatty acid esters and/or polyglycerol fatty acid esters. Also included are nonionic surface active agents having HLB values of from 2 to 6. Polymeric materials useful as dispersants include the various cellulose ethers, such as ethyl cellulose, methyl cellulose, hydroxyethyl cellulose, hydroxypropyl cellulose, carboxyethyl cellulose and combinations thereof. Preferably, such cellulose ethers will be provided at a concentration of from 0.1 to 2 weight percent, based on the weight of the monomer, more preferably 0.5 weight percent based on the weight of the monomer. Other useful materials include the hydrophobic clays such as cationic surfactant treated bentonite clays. The preferred dispersing agent is a mixture of a fumed hydrophobic silica (such as AEROSIL™ R-972 fumed silica manufactured by Degussa, Inc.) and a copolymer of lauryl methacrylate and acrylic acid. In a preferred copolymer, the mole ratio of lauryl methacrylate to acrylic acid in the copolymer is 99 to 1.

As indicated above, a key element of the invention is the wrinkling and the other surface and internal characteristics of the polymer particles as shown in FIGS. 1–4. Such wrinkling is attributable to crosslinking of the monomer droplet in the vicinity of its surface. Introducing the wrinkling and high surface characteristics to the particles of the invention is thought to be related to at least the process of the invention which requires the utilization of an initiator system that is at least partially oil phase soluble. Preferably, a redox system is employed which comprises, as a reducing component thereof, an at least partially oil phase soluble material. "Partially soluble in the organic liquid phase" is defined to mean possessing sufficient solubility in the oil phase to yield polymer particles as depicted in any of FIGS. 1–4. Preferably, the reducing agent will partition such as to provide between 10 and 2500 ppm reducing agent in the oil phase, more preferable at least 100 ppm reducing agent in the oil phase. Suitable oxidizing components include, for example, t-butyl hydroperoxide (t-BHP); 2,5-dihydroperoxy-2,5-dimethylhexane; and cumene hydroperoxide. A preferred reducing component of the redox system is sulfur dioxide gas. Thermal initiators that have sufficient oil phase solubility, such as VAZO™ 64 azobisisobutyronitrile available from DuPont and benzoyl peroxide are also suitable.

In the process of the invention, the monomer mixture is suspended in the inert oil phase, typically utilizing agitation, to form monomer mixture droplets. The monomer droplets must be large enough such that the wrinkling characteristic imparted to the particles is useful, for example, in increasing absorbency rate when employed in a personal care product. As is well-known in the art, variation of agitation intensity and shear may be used to control monomer droplet size. Generally preferred is a droplet size of on the order of greater than 75 micrometers. Maintaining proper droplet size requires limiting agitator speed, generally to less than that utilized in the prior art, depending upon blade design and other equipment limitations.

The reaction is carried out at any convenient temperature at which the initiator system operates efficiently. Thus, in the preferred t-butyl hydroperoxide/$SO_2$ system, the temperature of reaction may range from less than room temperature to 90° C. Preferably the reaction is initiated at room temperature or lower, preferably about 20° C.; proceeds adiabatically (to a temperature between 55° C. to 65° C.); and optionally includes a final temperature increase to 75° C. The reaction is initiated by bubbling the reducing agent, such as sulfur dioxide, into the reaction mixture.

The rate of initiation should be such as to lead to an efficient polymerization without compromising polymer properties. Excessively fast rates of initiation lead to shorter polymer chain lengths and inferior polymer properties. The rate of initiation may be adjusted by increasing or decreasing the flow rate of the reducing agent (to increase or decrease the rate of initiation, respectively). Preferred flow rates are a function of the reactor system employed and may be determined by conventional means. For the 2-liter reaction systems described in the examples and for reducing agents comprising a 0.1 percent mixture of sulfur dioxide in nitrogen, suitable reducing agent flow rates are between 200 and 1000 mL/min. An especially preferred reducing agent flow rate under such conditions is 750 mL/min.

After the polymerization reaction is finished, the polymer product is recovered by removing the inert oil phase and drying. The dried, finished product may then be treated with a wetting agent, such as VORANOL® 2070 polyol, manufactured by The Dow Chemical Company. The wetting agent helps overcome the adverse effect of any remaining dispersing agent, such as hydrophobic inert inorganic silica material, remaining on the finished product. Preferably, the dry polymer beads will be provided with 0.25 to 2 weight percent wetting agent based on the weight of the dry beads, more preferably 0.5 to 1.5 weight percent. More preferably, 1 weight percent wetting agent based on the weight of dry polymer will be provided.

In characterizing the finished water-absorbent polymers of the invention, swelling capacity under pressure (SCUP), centrifuge capacity, vortex rate, swell time, and surface area are measured. Preferred polymers will have a low vortex rate and swell time and a high SCUP and swelling capacity.

Swelling capacity under pressure is closely related to the modulus of a polymer. SCUP measures the ability of a polymer to swell against a pressure of 0.29 psi (2 kPa) which pressure simulates the pressures that the polymer must swell against in a disposable infant diaper. In the test procedure, 0.160 gram of the polymer of interest is placed in a cylinder including a Whatman GF-A filter paper resting on a 100 mesh (149 micrometers) screen. A loose fitting cover is placed on top of the polymer and a 100 gram weight is placed on top of the cover. The polymer is exposed to 0.9 percent NaCl solution by means of an apparatus that maintains the level of the saline reservoir such that there is no hydrostatic head pressure. The amount of liquid absorbed with 30 seconds, 5 minutes, and 60 minutes is measured. Preferred 5 minute SCUP values are greater than 10 grams saline solution/gram polymer, are more preferably greater than 13 grams saline solution/gram polymer, are even more preferably greater than 15 grams, and are most preferably greater than 20 grams saline solution/gram polymer.

The centrifuge capacity of the product of the invention is determined using the following procedure. A pulverized sample of dry polymer is screened to pass through a 30-mesh (500 micrometers) screen but to be retained on a 50-mesh (300 micrometers) screen. A 0.2 gram portion of this material is evenly placed in a 64 mm by 57 mm bag of a non-woven fabric shaped like a tea bag. The bag containing the test material is immersed in a 0.9 percent sodium chloride saline solution for thirty minutes, removed from the solution, centrifuged at a speed of 1500 rpm for 3 minutes, removed from the centrifuge and weighed. Centrifuge capacity is calculated as $[(W_3-B_1)-(W_2-W_1)]/(W_2-W_1)$, where $W_1$ is the weight of an empty dry tea bag, $W_2$ is the weight of an empty dry tea bag containing the sample, $W_3$ is the weight of the wet centrifuged sample and tea bag, and $B_1$ is the average weight of a wet centrifuged tea bag. Preferred centrifuge capacities are greater than 10 grams saline solution/gram polymer, are more preferably greater than 15 grams saline solution/gram polymer, are even more preferably greater than 20 grams saline solution/gram polymer, and are most preferably greater than 25 grams saline solution/gram polymer.

The rate at which the polymers of interest will absorb aqueous fluid is a key advantage of the invention. It is characterized by a "vortex rate" test. This test measures and reports in seconds the time required for a vortex generated by a magnetic stir in a container to disappear when 2 grams of absorbent polymer are added to 50 milliliters of 0.9 percent saline solution. Preferred vortex rates are less than 65 seconds, are more preferably less than 40 seconds, and are even more preferably less than 20 seconds.

The swell rate of the polymer is determined using the following procedure. A pulverized sample of the dry polymer is screened to pass through a 30-mesh (500 micrometers) screen, but to be retained on a 50-mesh (300 micrometers) screen. A 1.0 gram portion of this material is placed into a weighing boat. To the boat, 30.0 grams of a 0.9 percent sodium chloride saline solution is rapidly added. The swell time equals the time it takes for the sample to swell to form a continuous barrier atop the surface of the saline solution. Preferred swell times are less than one minute, are more preferably less than 35 seconds, and are even more preferably less than 25 seconds, and are most preferably less than 10 seconds.

The polymers of the invention may be utilized as a principal absorbing component of a personal care product. A typical such product is a disposable diaper wherein the polymer of the invention is contained in a composite structure generally comprising an exterior impervious sheet and a porous interior sheet, with the polymer of the invention, typically mixed with cellulose fibers, sandwiched between said sheets.

Other absorbent structures into which the polymers of the invention may be utilized include incontinence devices, sanitary napkins, paper towels, and facial tissues.

The following examples illustrate the products and process of the invention. It is not intended that the invention be limited to their scope.

EXAMPLE 1

Preparation of Wrinkled Particles of the Invention
(29 Percent Acrylic Acid in the Aqueous Phase,
Neutralized to 85.3 Percent Na Salt)

Figure 1B:
FIG. 1(b) is a photomicrograph of the particles of 1(a) in a cross section at a magnification of 50.
Figure 2A:
FIG. 2(a) is a photomicrograph at 50 magnification of the polymer particles of the invention wherein the initial monomer mixture comprises 26 percent acrylic acid.
Figure 2B:
FIG. 2(b) is a photomicrograph at 50 magnification showing the particles of FIG. 2(a) in cross section.
Figure 3A:
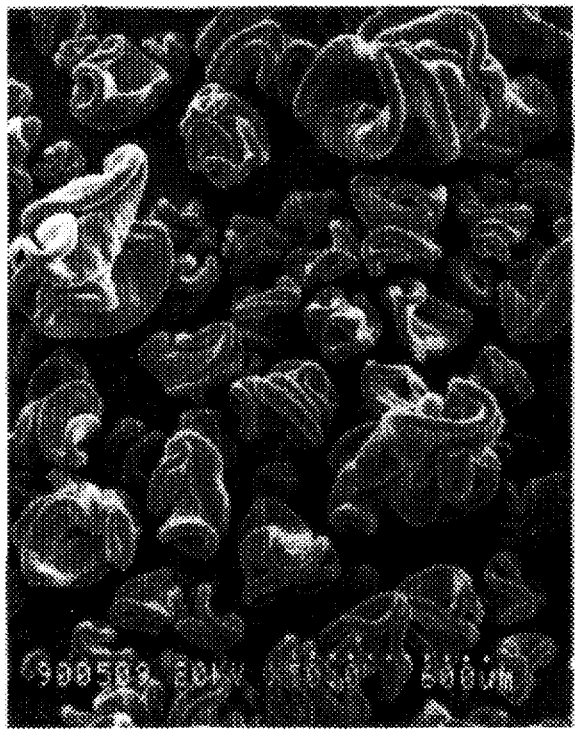
FIG. 3(a) is a photomicrograph at 50 magnification showing the polymer particles of the invention wherein the initial monomer concentration of the polymerization mixture is 29 percent acrylic acid.
Figure 3B:
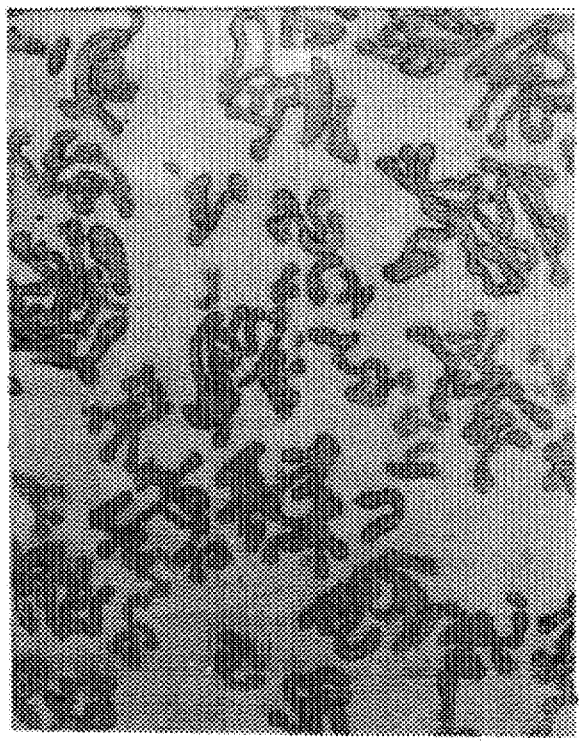
FIG. 3(b) is a photomicrograph at a magnification of 50 showing the particles of FIG. 3(a) in cross section.
Figure 4A:
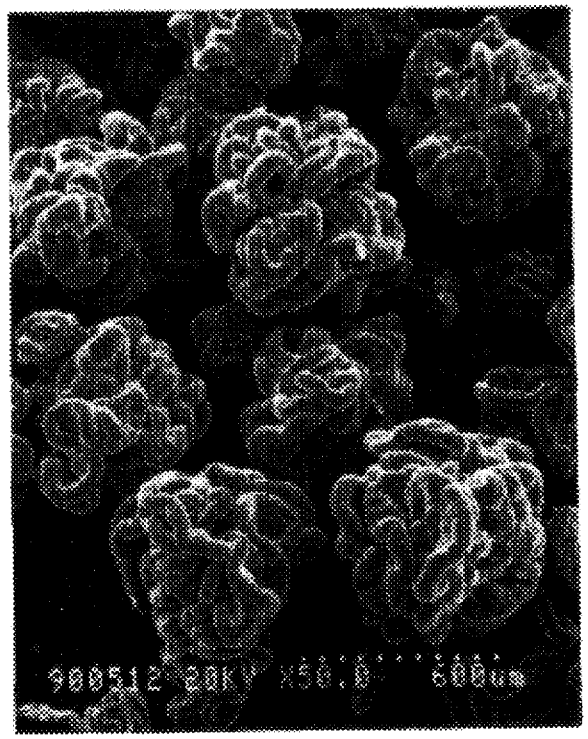
FIG. 4(a) is a photomicrograph at a magnification of 50 showing the polymer particles of the invention wherein the initial monomer concentration is 33 percent acrylic acid.
Figure 4B:
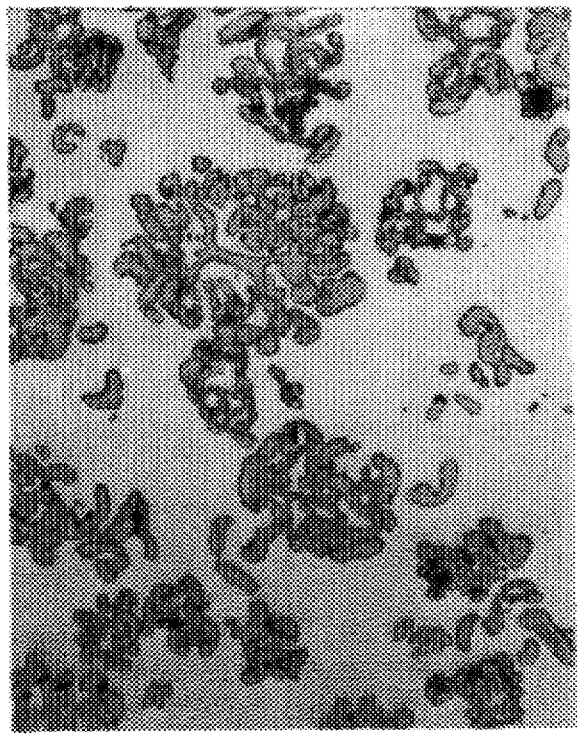
FIG. 4(b) is a photomicrograph at a magnification of 50 showing the polymer particles of FIG. 4(a) in cross section.

To 116 grams of acrylic acid is added 100 grams of a 50 percent aqueous solution of sodium hydroxide, 0.23 grams of methylene-bis-acrylamide (an aqueous phase soluble crosslinking agent), 0.46 grams (4000 ppm) of trimethylolpropane triacrylate (an oil phase soluble crosslinking agent), 183 grams of water, and 0.46 grams of VERSENEX 80® chelating agent, of The Dow Chemical Company. The Referring to FIGS. 1–4, the wrinkled polymer particles, as a function of percent acrylic acid in the monomer mixtures, are shown. The paired photomicrographs at 50 magnification show the wrinkled polymer particles of the invention for 24 percent initial acrylic acid monomer mixture concentration in FIG. 1(a). The same polymer particles are shown in FIG. 1(b) wherein the particles have been immobilized and cross-sectioned. Considering the Figures together, it is seen that the degree of wrinkling and internal complexity of the structure of the polymer particles of the invention increase with increasing concentration of monomer.

TABLE I

| EXAMPLE NO. | % ACRYLIC ACID | ACRYLIC ACID (g) | 50% NaOH (g) | VERSENEX 80 ® CHELATING AGENT (g) | METHYLENE BIS-ACRYLAMIDE (g) | TRIMETHYLOL PROPANE TRIACETIC ACID (g) |
|---|---|---|---|---|---|---|
| 1 | 29 | 116 | 110 | 0.46 | 0.23 | 0.46 |
| 2 | 24 | 96 | 91 | 0.38 | 0.19 | 0.38 |
| 3 | 26 | 104 | 98 | 0.41 | 0.21 | 0.41 |
| 4 | 33 | 132 | 125 | 0.52 | 0.26 | 0.52 |

TABLE II

WRINKLED POLYMER PARTICLES OF THE INVENTION USING t-BUTYL HYDROPEROXIDE AS INITIATOR

| EXAMPLE NO. | % ACRYLIC ACID | 30 SEC. SCUP (g/g) | 5 MIN. SCUP (g/g) | 60 MIN. SCUP (g/g) | CENT. CAP. (g/g) | VORTEX (sec) | SWELL TIME (sec) | SURFACE AREA ($m^2/g$) |
|---|---|---|---|---|---|---|---|---|
| 1 | 29 | 8.5 | 20.6 | 22.5 | 20.5 | 9.4 | 9 | 0.32 |
| 2 | 24 | 7.4 | 22.9 | 25.8 | 28.5 | 18.2 | 21.3 | 0.45 |
| 3 | 26 | 8.3 | 25.3 | 26.3 | 25.4 | 10.3 | 11.7 | 0.26 |
| 4 | 33 | 4.1 | 14.4 | 17.2 | 15.5 | 18.9 | 20.1 | 0.32 | monomer mix is cooled to 25° C. and added to a mixture of 0.6 grams of AEROSIL™ R-972 fumed hydrophobic silica of Degussa, Inc., 0.32 grams of a copolymer of laurylmethacrylate and acrylic acid in a weight ratio of 99:1 as a dispersing agent, and 800 grams of ISOPAR® M deodorized kerosene of Exxon in a 2 liter reactor. The reactor is equipped with a 4-bladed agitator rotating at 250 rpm. Then 0.089 grams of 70 percent t-butyl hydroperoxide (t-BHP) is added. The suspension is purged for 30 minutes with nitrogen and then heated to 50° C. At 45° C., the polymerization is initiated by bubbling into the suspension of 0–1 weight percent a dilute stream of sulfur dioxide in nitrogen at a flow rate between 200 mL/min and 1000 mL/min. The reaction temperature adiabatically rises to 55° C. After the polymerization is complete, the reaction mixture is heated at 75° C. for one hour. The ISOPAR® deodorized kerosene is removed by filtration and the polymer product of the invention dried in an oven. When dry, as optional steps, the polymer is slurried in methanol and 0.58 grams of VORANOL® 2070 polyol wetting agent of The Dow Chemical Company is added. The methanol is removed by vacuum stripping at 50° C. The wrinkled polymer particles of the invention are characterized in Table II and FIG. 3.

EXAMPLES 2–4

Polymerizations identical to Example 1 are run at other acrylic acid monomer concentrations. The recipes for those examples appear in Table I. These wrinkled polymer particles of the invention are characterized in Table II and FIGS. 1, 2 and 4.

Comparative Example A

The polymerization of Example 1 is repeated with regard to process and reaction components, except the initiator system is of the prior art. In this experiment, the t-BHP oil phase soluble oxidizing component of the redox initiator system of the invention is replaced with an aqueous soluble oxidizing component. Thus, 0.86 gram of sodium persulfate is added to the aqueous reaction mixture before the mixture is added to the ISOPAR® M deodorized kerosene oil phase. The persulfate initiates the polymerization at 45° C. and the reaction is allowed to proceed adiabatically at 55° C. for 2 hours, followed by an additional one hour heating at 75° C.

Figure 5:
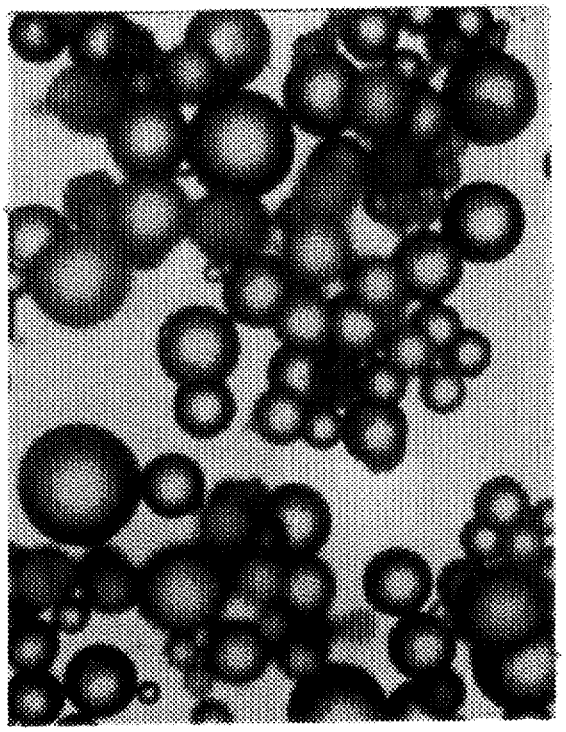
FIG. 5 is a photomicrograph at a magnification of 50 showing the polymer particles of Comparative Example A, representative of the prior art.

The product produced by the process of Comparative Example A is substantially spherical in shape and round in cross section, as shown in FIG. 5. The vortex rate for the spherical beads is 145 seconds.

Comparing the vortex rate results of the Examples 1 through 4 products of the invention reported at Table II with that of Comparative Example A shows that the present invention compositions achieve significantly superior absorbency rates of 9 to 21 seconds. Thus, the products of the invention are 7 to 16 times faster than Comparative Example A, characteristic of the prior art.

EXAMPLES 5 AND 6

The process of Example 1 is repeated except that 2,5-dihydroperoxy-2,5dimethylhexane is substituted for t-BHP as the oxidizing component of the redox initiator system. The wrinkled polymer particles of the invention are characterized in Table III.

TABLE III

WRINKLED POLYMER PARTICLES OF THE INVENTION USING 2,5-DIHYDROPEROXY-2,5-DIMETHYLHEXANE AS INITIATOR

| SAMPLE NO. | 30 SEC. SCUP (g/g) | 5 MIN. SCUP (g/g) | 60 MIN. SCUP (g/g) | CENT. CAP. (g/g) | VORTEX RATE (sec) | SWELL TIME (sec) |
|---|---|---|---|---|---|---|
| 5 | 7.4 | 15.5 | 15.9 | 18.7 | 22.0 | 25.3 |
| 6 | 3.8 | 13.4 | 14.4 | 17.7 | 20.0 | 21.7 |

EXAMPLES 7-9

The process of Example 1 is repeated except that cumene hydroperoxide is substituted for t-BHP as the oxidizing component of the redox initiator system. The wrinkled polymer particles of the invention are characterized in Table IV.

TABLE IV

WRINKLED POLYMER BEADS OF THE INVENTION USING CUMENE HYDROPEROXIDE AS INITIATOR

| SAMPLE NO. | 30 SEC. SCUP (g/g) | 5 MIN. SCUP (g/g) | 60 MIN. SCUP (g/g) | CENT. CAP. (g/g) | VORTEX RATE (sec) | SWELL TIME (sec) |
|---|---|---|---|---|---|---|
| 7 | 8.1 | 25.3 | 26.8 | 25.3 | 32.0 | 33.5 |
| 8 | 5.5 | 25.2 | 27.8 | 27.0 | 41.0 | 34.5 |
| 9 | 3.2 | 19.9 | 26.1 | 28.4 | 64.0 | 62.9 |

EXAMPLE 10

Preparation of Polymer Particles of the Invention Including Graftable Monomers in the Monomer Mixture (29 Percent Acrylic Acid, in the Aqueous Phase, Neutralized to 85.3 Percent Na Salt)

To 116 grams of acrylic acid are added 110 grams of sodium hydroxide, 0.93 gram of diethylene glycol diacrylate, 0.46 (4000 ppm) gram of trimethylolpropane triacrylate (TMPTA), 183 grams of water containing 5.0 grams of AIRVOL™ 107 (polyvinyl alcohol), and 0.46 gram of VERSENEX® 80. The monomer mix is cooled to 25° C. and added to a mixture of 0.6 gram of AEROSIL™ R-972 fumed hydrophobic silica, 0.32 gram of a copolymer of laurylmethacrylate and acrylic acid and 800 grams of ISOPAR® M deodorized kerosene in a 2 liter reactor. The reactor is equipped with a 4-bladed agitator rotating at 250 rpm. Then 0.089 gram of 70 percent t-butyl hydroperoxide is added. The suspension is purged for 30 minutes with nitrogen and then heated to 50° C. At 25° C., the polymerization is initiated by bubbling in a dilute steam of sulfur dioxide in nitrogen. The reaction temperature proceeds adiabatically at 55° C. After the polymerization is complete, the reaction mixture is heated at 75° C. for one hour. The ISOPAR® deodorized kerosene is removed by filtration and the polymer product dried in an oven. When dry, the polymer is, as an optional treatment, slurried in methanol and 0.58 gram of VORANOL® 2070 polyol wetting agent is added. The methanol is removed by vacuum stripping at 50° C.

The product is characterized by a vortex rate of 14 seconds.

EXAMPLE 11

Preparation of Wrinkled Particles of the Invention (31.6 Percent Acrylic Acid in the Aqueous Phase, Neutralized to 80 Percent Sodium Salt)

To 126.4 grams of acrylic acid is added 112.26 grams of a 50 percent aqueous solution of sodium hydroxide. 1.74 grams (4000 ppm) of trimethylolpropane triacrylate (an oil phase soluble crosslinking agent), 155.19 grams of water, and 0.46 grams of VERSENEX 80® chelating agent, of The Dow Chemical Company. The monomer mix is cooled to 25° C. and added to a mixture of 0.6 grams of AEROSIL™ R-972 fumed hydrophobic silica of Degussa, Inc., 0.32 grams of a copolymer of laurylmethacrylate and acrylic acid in a weight ratio of 99:1 as a dispersing agent, and 800 grams of ISOPAR® M deodorized kerosene of Exxon in a 2 liter reactor. The reactor is equipped with a 4-bladed agitator rotating at 250 rpm. Then, 0.9 grams of 7 percent t-butyl hydroperoxide (t-BHP) is added. The suspension is purged for 30 minutes with nitrogen and then heated to 50° C. At 45° C., the polymerization is initiated by bubbling into the suspension a dilute stream of 0.1 weight percent sulfur dioxide in nitrogen at a flow rate of 750 mL/min. The reaction temperature adiabatically rises to 55° C. After the polymerization is complete, the reaction mixture is heated at 75° C. for one hour. The ISOPAR® deodorized kerosene is removed by filtration and the polymer product of the invention is dried in an oven. When dry, as optional steps, the polymer is slurried in methanol and 1 weight percent of VORANOL® 2070 polyol wetting agent of The Dow Chemical Company based on the weight of the dry polymer is added. The methanol is removed by vacuum stripping at 50° C. The polymer produced exhibits a 30 second SCUP of 5.2, a 5 minute SCUP of 7.5, a 60 minute SCUP of 23.4, a centrifuge capacity of 32.3 grams/gram and a vortex rate of 13.5 seconds.

EXAMPLE 12

Preparation of Wrinkled Particles of the Invention (35 Percent Acrylic Acid in the Aqueous Phase, Neutralized to 80 Percent Sodium Salt)

The procedure of Example 10 is repeated except that 140.0 grams acrylic acid, 124.34 grams of the 50 percent aqueous solution of sodium hydroxide, 128.85 grams water, 0.193 grams trimethylolpropane triacrylate, and 0.5 grams of the 7 percent t-butyl hydroperoxide (t-BHP) are utilized rather than the amounts set forth in Example 10. The polymer produced exhibits a 30 second SCUP of 11.6, a 5 minute SCUP of 24.7, a 60 minute SCUP of 26.3, a centrifuge capacity of 24.6 grams/gram and a vortex rate of 18.0 seconds.

EXAMPLE 13

Preparation of Polymer Particles of the Invention Including Graftable Monomers in the Monomer Mixture (27 Percent Acrylic Acid, in the Aqueous Phase, Neutralized to 75 Percent Na Salt)

To 108 grams of acrylic acid are added 89.93 grams of a 50 percent aqueous solution of sodium hydroxide, 0.54 gram of tetraethyleneglycol diacrylate, 4.64 (43000 ppm) gram of trimethylolpropane triacrylate (TMPTA), 184 grams of water containing 32.1 grams of a 15 percent solution of AIRVOL™ 107 polyvinyl alcohol of Air Products, and 0.46 gram of VERSENEX® 80 chelating agent. The monomer mix is cooled to 25° C. and added to a mixture of 0.6 gram of AEROSIL™ R-972 fumed hydrophobic silica of Degussa, Inc., 0.32 gram of a copolymer of lauryl methacrylate and acrylic acid and 800 grams of ISOPAR® M deodorized kerosene in a 2 liter reactor. The reactor is equipped with a 4-bladed agitator rotating at 250 rpm. Then 0.39 gram of 7 percent t-butyl hydroperoxide is added. The suspension is purged for 30 minutes with nitrogen and then heated to 50° C. At 25° C., the polymerization is initiated by bubbling in a dilute stream of sulfur dioxide in nitrogen at a rate of 750 mL/min. The reaction temperature proceeds adiabatically to 55° C. After the polymerization is complete, the reaction mixture is heated at 75° C. for one hour. The ISOPAR® M deodorized kerosene is removed by filtration and the polymer product dried in an oven. When dry, the polymer is, as an optional treatment, slurried in methanol and 1 weight percent VORANOL® 2070 polyol wetting agent based on the weight of the dry polymer is added. The methanol is removed by vacuum stripping at 50° C.

The product is characterized by a 30 second SCUP of 3.6, a 5 minute SCUP of 10, a 60 minute SCUP of 27, a centrifuge capacity of 31 grams/gram and a vortex rate of 29 seconds.

EXAMPLE 14

Preparation of Polymer Particles of the Invention Including Graftable Monomers in the Monomer Mixture (35 Percent Acrylic Acid, in the Aqueous Phase, Neutralized to 75 Percent Na Salt)

The procedure off Example 12 is repeated except that 140.0 grams acrylic acid, 116.57 grams of the 50 percent aqueous solution of sodium hydroxide, 95.01 grams water, 0.58 grams trimethylolpropane triacrylate, 41.61 grams of a 15 percent solution of AIRVOL™ 107 polyvinyl alcohol and 0.25 grams of the 7 percent t-butyl hydroperoxide (t-BHP) are utilized rather than the amounts set forth in Example 12. Further, in this example no second crosslinking agent, i.e., tetraethyleneglycol diacrylate, is used. The polymer produced exhibits a 30 second SCUP of 2.1, a 5 minute SCUP of 22, a 60 minute SCUP of 24, a centrifuge capacity of 22 grams/gram and a vortex rate of 24 seconds.

What is claimed is:

1. A fluid absorbent polymer having a fast rate of absorption, comprising:

individual non-agglomerated polymer particles, each said particle having a mean surface area greater than about 0.2 m²/g, each said particle having a surface substantially continuous but including a plurality of wrinkles comprising folds, ridges, crevices and channels.

2. The polymer of claim 1, wherein said individual non-agglomerated polymer particles have a mean surface area between about 0.2 and about 0.5 m²/g.

3. The polymer of claim 3, wherein said individual non-agglomerated polymer particles have a mean surface area of about 0.3 m²/g.

4. The polymer of either of claims 1 or 2, wherein said polymer is the polymerization product of a water-soluble ethylenically unsaturated monomer mixture or salt thereof.

5. The polymer of claim 4, wherein said ethylenically unsaturated monomer mixture or salt thereof comprises an amide, carboxylic acid or its esters, vinyl amine, or salt or mixture thereof.

6. The polymer of claim 5, wherein said ethylenically unsaturated monomer mixture or salt thereof comprises acrylic acid, sodium acrylate or mixture thereof, said polymer being crosslinked with a polyvinyl monomer.

7. The polymer of claim 5, wherein said monomer mixture includes a monomer capable of graft polymerizing with at least one other component of said monomer mixture.

8. The polymer of claim 7, wherein said monomer capable of graft polymerizing with at least one other component of said monomer mixture is polyvinyl alcohol.

9. The polymer of either of claims 1 or 2, wherein said individual non-agglomerated polymer particles have a mean diameter greater than about 75 microns.

10. The polymer of claim 9, wherein said polymer has a vortex rate of absorption less than about 60 seconds.

11. The polymer of either of claims 1 or 2, wherein said individual non-agglomerated polymer particles have a mean diameter between about 150 and about 1000 microns.

12. The polymer of either of claims 1 or 2, wherein said individual non-agglomerated polymer particles have a mean diameter of about 400 microns.

13. The polymer of either of claims 1 or 2, further comprising a wetting agent.

14. The polymer of claim 13, wherein said wetting agent is a polyol.

15. A process for making a fluid absorbent polymer having a fast rate of absorption, comprising:

suspending an aqueous mixture of a water soluble monomer in a continuous, inert organic liquid phase containing a dispersing agent with agitation such that droplets of said aqueous mixture form in said continuous phase;

adding to said suspension an oxidizing component of a redox initiator pair, said oxidizing component at least partially soluble in the organic liquid phase; and introducing a reducing component of said redox pair into said organic phase under polymerizing conditions at a controlled rate such that said polymer particles having wrinkled surfaces form.

16. The process of claim 15, wherein said droplets have a mean diameter greater than about 75 microns.

17. The process of claim 15, wherein said droplets have a mean diameter between about 150 and about 1000 microns.

18. The process of claim 15, wherein the droplets have a mean diameter of about 400 microns.

19. The process of any of claims 16, 17, or 18, wherein said dispersing agent is a cellulose ether, said cellulose ether being provided in an amount of about 0.5 weight percent based on the weight of the water soluble monomer.

20. The process of any of claims 16, 17, or 18, wherein said dispersing agent is a nonionic surface active composition having a HLB value of from about 2 to about 6.

21. The process of any of claims 16, 17, or 18, wherein said dispersing agent in a mixture of hydrophobic silica and a copolymer of lauryl methacrylate and acrylic acid in a weight ratio of about 99 parts by weight lauryl methacrylate to about 1 part by weight acrylic acid.

22. The process of claim 21, further comprising treating said polymer particles with a wetting agent.

23. The process of any of claims 16, 17, or 18, wherein said water soluble monomer comprises an ethylenically unsaturated monomer and crosslinker therefor, said ethylenically unsaturated monomer being at least partially neutralized by a basic material.

24. The process of claim 23, wherein said ethylenically unsaturated monomer is an amide carboxylic acid or its esters, vinyl amine, or salt or mixture thereof.

25. The process of claim 23, wherein said ethylenically unsaturated monomer is acrylic acid.

26. The process of claim 23, wherein said ethylenically unsaturated monomer is neutralized to a degree of about 75 to about 95 percent by said basic material.

27. The process of claim 23, wherein said ethylenically unsaturated monomer is neutralized to a degree of about 80 to about 90 percent by said basic material.

28. The process of claim 23, wherein said crosslinker is metheylene-bisacrylamide, diethylene glycol diacrylate, tetraethyleneglycol diacrylate, trimetholpropane triacrylate, or mixtures thereof.

29. The process of claim 23, wherein said oxidizing component is t-butyl hydroperoxide, cumene hydroperoxide, or 2,5-dihydroperoxy-2,5-dimethylhexane.

30. The process of claim 23, wherein said reducing component is sulfur dioxide.

31. A polymer produced in accordance with the process of claim 23.

32. The polymer of claim 31, wherein said ethylenically unsaturated monomer is acrylic acid.

33. A method for using the polymer of claim 1 comprising retaining said polymer between a fluid impervious bottom layer and a fluid pervious top layer.

34. The method of claim 33, wherein said individual non-agglomerated polymer particles have a mean surface area between about 0.2 and about 0.5 $m^2/g$.

35. A method for using the polymer produced in accordance with the process of claim 16 comprising retaining said polymer between a fluid impervious bottom layer and a fluid pervious top layer.

36. The method of claim 35, wherein said droplets have a mean diameter greater than about 75 microns.

37. The method of claim 35, wherein said droplets have a mean diameter between about 150 and about 1000 microns.

38. The method of claim 35, wherein said droplets have a mean diameter of about 400 microns.

39. A polymer having a fast rate of aqueous fluid absorption comprising individual non-agglomerated polymer particles, each said particle having a mean surface area of between about 0.2 and 0.5 $m^2/g$, a mean diameter greater than about 75 microns, and a surface which is substantially continuous but including a plurality of wrinkles, comprising folds, ridges, crevices and channels, the polymer comprising polymerized units of one or more water-soluble ethylenically unsaturated monomers or salts thereof, and one or more crosslinking monomers.

* * * * *

UNITED STATES PATENT AND TRADEMARK OFFICE
CERTIFICATE OF CORRECTION

PATENT NO.   : 5,744,564

DATED        : April 28, 1998

INVENTOR(S)  : Frederick W. Stanley, Jr., deceased; late of Midland, by
Caroline Stanley, legal rep.; Jack C. Lamphere; Larry R. Wilson It is certified that error appears in the above-identified patent and that said Letters Patent is hereby corrected as shown below:

Col. 14, line 8, "claim 3" should read -- claim 2 --.

Signed and Sealed this

Second Day of February, 1999

Attest:

Attesting Officer

*Acting Commissioner of Patents and Trademarks*